(12) United States Patent
Inderbitzen et al.

(10) Patent No.: US 8,142,468 B2
(45) Date of Patent: Mar. 27, 2012

(54) GUIDEWIRE WITH DISTAL EXPANSION FEATURE AND METHOD FOR ENHANCING THE DELIVERABILITY AND CROSSABILITY OF MEDICAL DEVICES

(75) Inventors: Mark N. Inderbitzen, Hypoluxo, FL (US); Robert Burgermeister, Bridgewater, NJ (US); Kirk L. Johnson, Weston, FL (US)

(73) Assignee: Cordis Corporation, Miami Lakes, FL (US)

( * ) Notice: Subject to any disclaimer, the term of this patent is extended or adjusted under 35 U.S.C. 154(b) by 877 days.

(21) Appl. No.: 11/316,446

(22) Filed: Dec. 22, 2005

(65) Prior Publication Data

US 2007/0149898 A1 Jun. 28, 2007

(51) Int. Cl.
*A61M 29/00* (2006.01)

(52) U.S. Cl. .................................. 606/191; 604/165.02

(58) Field of Classification Search .................. 600/585; 623/1.11; 604/164.04, 165.01–165.04; 606/191
See application file for complete search history.

(56) References Cited

U.S. PATENT DOCUMENTS

| | | | |
|---|---|---|---|
| 4,932,959 A | 6/1990 | Horzewski et al. | |
| 5,061,273 A | 10/1991 | Yock | |
| 5,178,608 A * | 1/1993 | Winters | 604/102.02 |
| 5,265,622 A * | 11/1993 | Barbere | 600/585 |
| 5,273,052 A | 12/1993 | Kraus et al. | |
| 5,460,614 A | 10/1995 | Castaneda | |
| 5,497,782 A | 3/1996 | Fugoso | |
| 6,270,465 B1 | 8/2001 | Keith et al. | |
| 6,786,886 B2 * | 9/2004 | Miller et al. | 604/96.01 |
| 7,137,993 B2 * | 11/2006 | Acosta et al. | 623/1.11 |
| 2002/0072755 A1 * | 6/2002 | Bigus et al. | 606/108 |
| 2003/0229307 A1 | 12/2003 | Muni et al. | |
| 2004/0093061 A1 * | 5/2004 | Acosta et al. | 623/1.11 |
| 2005/0131343 A1 | 6/2005 | Abrams | |
| 2007/0021685 A1 * | 1/2007 | Oepen et al. | 600/585 |

FOREIGN PATENT DOCUMENTS

| | | |
|---|---|---|
| EP | 0551184 A | 7/1993 |
| WO | WO 91/04763 A | 4/1991 |

OTHER PUBLICATIONS

European Search Report dated Apr. 16, 2007 in EP Application 06256411.7.

* cited by examiner

*Primary Examiner* — Gary Jackson
*Assistant Examiner* — Katherine Dowe
(74) *Attorney, Agent, or Firm* — Cook Alex Ltd.

(57) ABSTRACT

A guidewire navigable through body vessels of a human subject for delivery of a catheter or the like is provided. The guidewire includes an expandable segment movable between a collapsed state and an expanded state. If the catheter encounters resistance in a vessel and cannot be advanced further, the medical professional can move the expandable segment to the expanded state in which the expandable segment engages an inner surface of the catheter. The expandable segment locks onto the catheter, which allows the guidewire and catheter to be advanced through the vessel together as a single unit. An inflatable balloon catheter movable along the guidewire requires only a single tube and is sealed by the expandable segment of the guidewire for subsequent inflation.

8 Claims, 3 Drawing Sheets

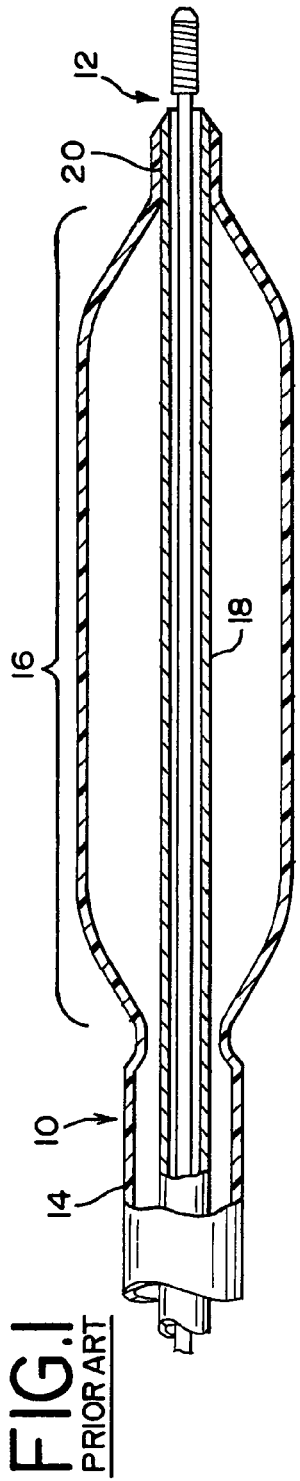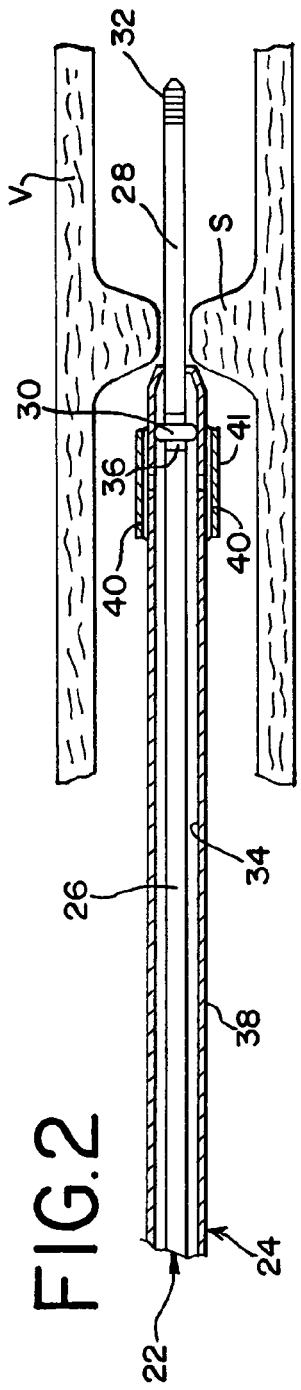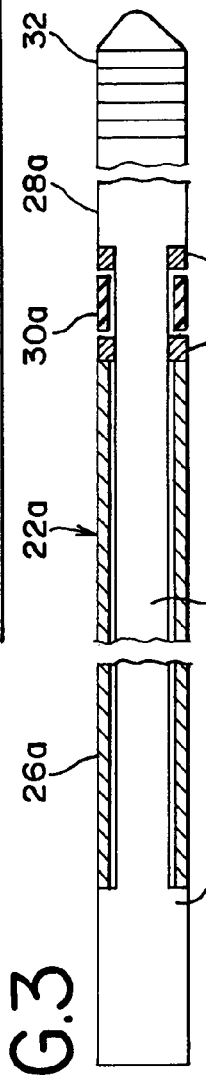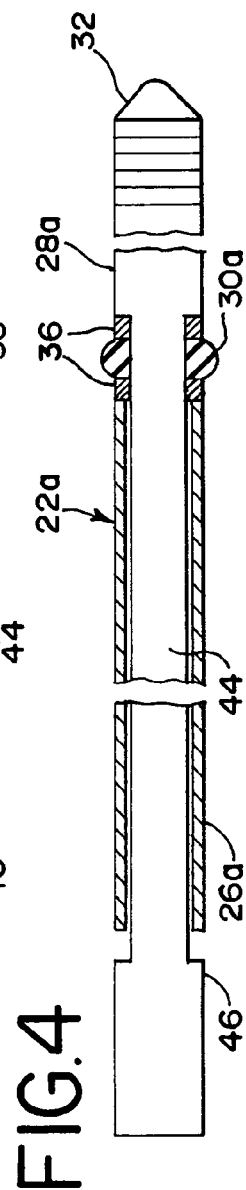

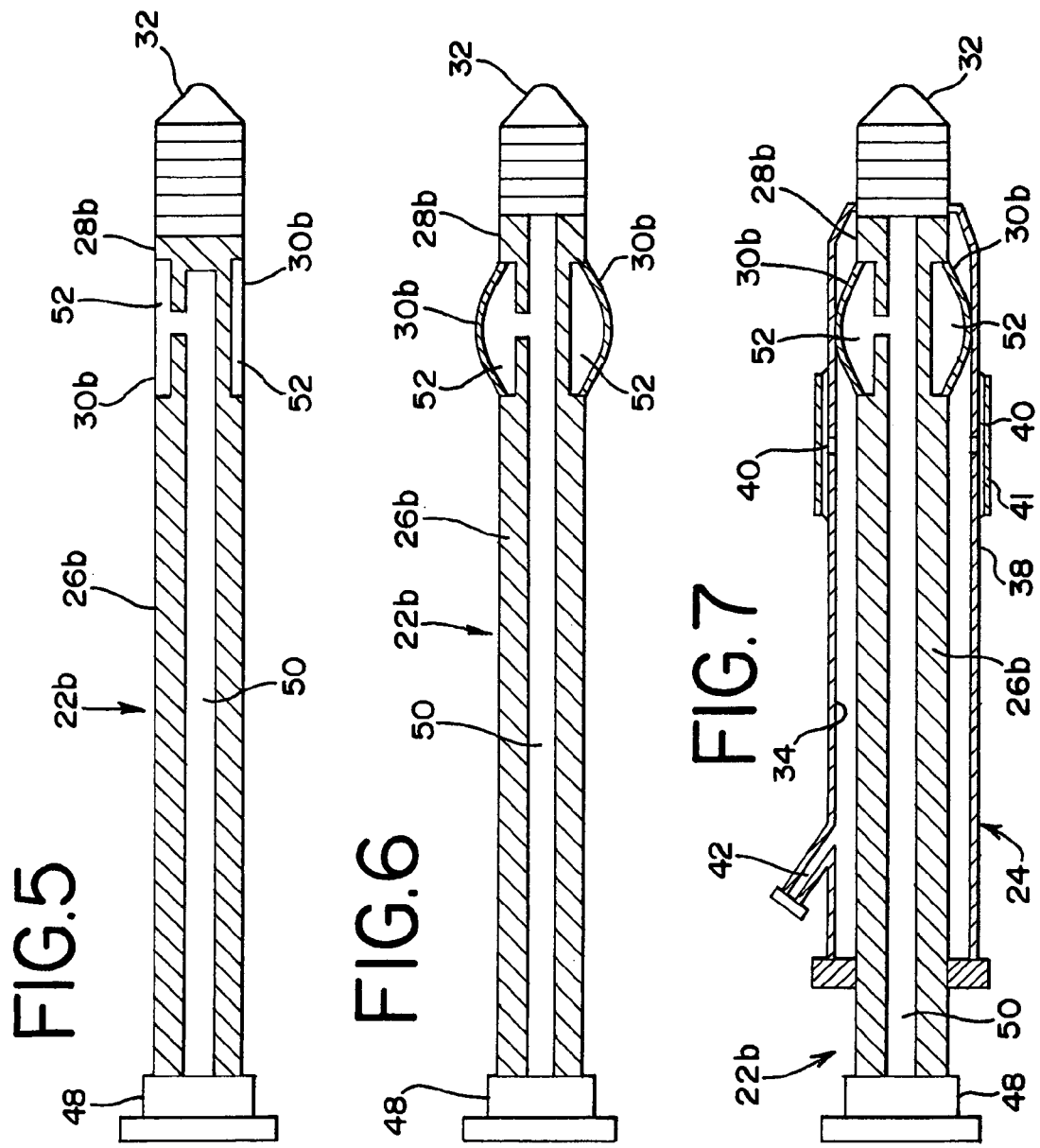

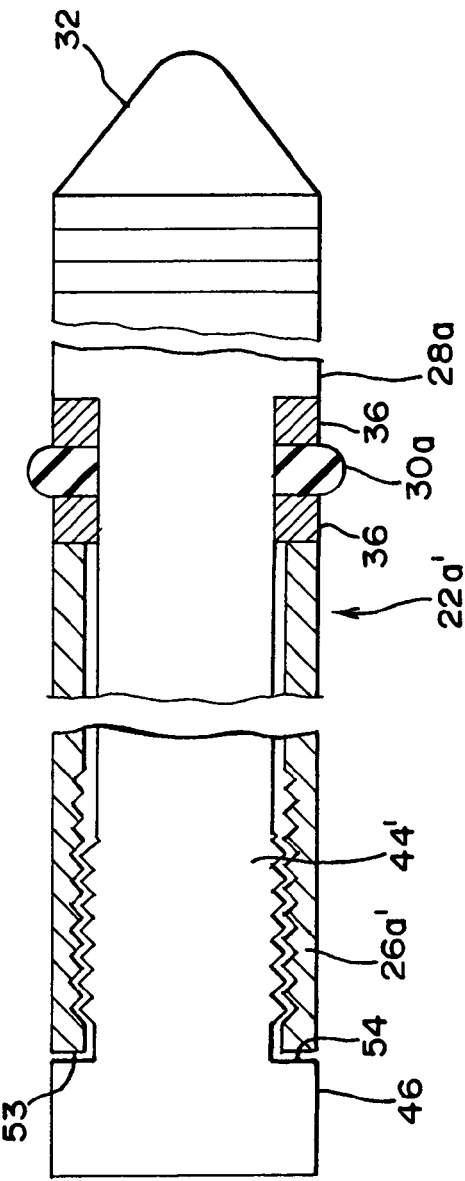
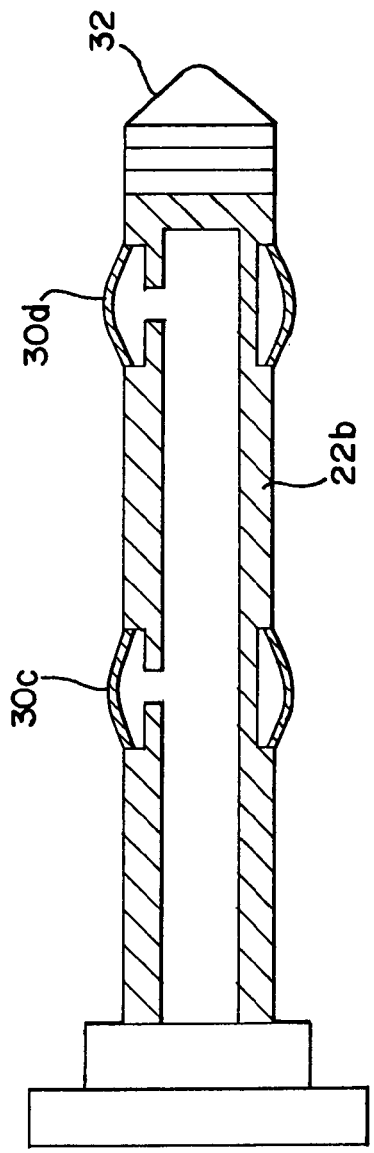
FIG. 8
FIG. 9

GUIDEWIRE WITH DISTAL EXPANSION FEATURE AND METHOD FOR ENHANCING THE DELIVERABILITY AND CROSSABILITY OF MEDICAL DEVICES

FIELD OF THE INVENTION

This invention generally relates to medical devices that are navigable through body vessels of a human subject. More particularly, this invention relates to guidewires used to position a catheter or the like within a body vessel.

DESCRIPTION OF RELATED ART

Vessel defects, such as blockages and stenoses, within the human vasculature system are often diagnosed and treated by the intraluminal delivery of diagnostic catheters, treatment fluids or expansion devices and stents. Expansion devices can take any of a number of forms, but are all generally delivered by a flexible catheter that, once properly positioned, deploys the expansion device. The path to the diseased site is typically tortuous and may additionally pass through other constricted lumens, so catheters cannot be used to define their own path through the vasculature. As such, a more rigid guidewire is first passed through the vasculature to the desired site, then the catheter is passed over the guidewire. A stent delivery system or catheter usable in such a procedure is commonly referred to as an "over-the-wire" or OTW catheter.

An alternative stent delivery system commonly referred to as a "rapid exchange" or RX catheter also uses a guidewire to properly position the distal end of a catheter. Examples of known RX catheters and methods of using the same are illustrated in U.S. Pat. No. 5,061,273 to Yock, which is hereby incorporated herein by reference.

Catheters must be flexible in order for them to follow the path defined by a guidewire through tortuous portions of the human anatomy. However, while catheters generally are capable of being pushed through tortuous paths, they cannot easily navigate an overly constricted vessel. When a catheter encounters resistance from a stenosed region of a vessel, rather than passing through, the downstream pushing force provided by an operator at the proximal end of the catheter is lost due to compression and "snaking" of the flexible catheter. Thereafter, the catheter must be backed out of the ostium to prevent further exasperation of the problem.

Another problem is that some stent delivery systems must be provided with an overly intricate construction in order to ensure proper operation, which increases the stiffness of the catheter. While this increased stiffness is useful in pressing the catheter through a stenosed region, it increases the diameter of the catheter and prevents the use of longer stents. Thus, rather than delivering a single elongated stent to a target site, the operator must instead deliver several shorter stents to the site.

For example, FIG. 1 illustrates a typical balloon catheter 10 on a typical guidewire 12, which catheter is subject to the above-described problem. The catheter 10 requires an outer tube 14 with an inflatable section 16 and an inner tube or inner body 18 to seal the inflatable section 16 at a distal portion 20. Further discussion of such a double-tube catheter can be found in U.S. Patent Application Publication No. 2003/0229307 to Muni et al., which is hereby incorporated herein by reference.

FIGS. 6 and 7 of that Muni et al. patent publication show an inner tubular member 15 having a thin wall section 22 which is said to collapse onto guidewire 18 to secure same into the catheter. This type of passive grasping feature creates a problem of not being able to reliably reverse the grasping action. Thus, to the extent the balloon 13 of that patent publication inflates to effect the passive grasping action, balloon deflation will not totally undo the grasping of the guidewire 18. A balloon catheter needing only a single tube could have a smaller diameter. This is useful in providing an inflatable section that is more flexible than a double-wall catheter. This flexibility facilitates delivery of longer stents which add a degree of bulk and stiffness. In addition, a grasping approach that avoids the disadvantages of a passive system such as in Muni et al. would be desirable.

Accordingly, a general aspect or object of the present invention is to provide a guidewire usable with standard catheters for navigation through a stenosed region of a body lumen.

Another aspect or object of this invention is to provide a guidewire facilitating the use of lower profile stent delivery systems.

Another aspect or object of this invention is to provide a method for navigating a medical device through a body vessel using a guidewire.

Another aspect or object of the present invention is to provide a guidewire and system that effects an active grasping action and that avoids the shortcomings of a passive grasping system.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with one aspect of the present invention, a guidewire is provided with an expandable segment movable between a collapsed state and an expanded state. In the collapsed state, the guidewire operates as a standard guidewire and facilitates the delivery of medical devices, such as stent delivery systems, to body vessels. If the medical device encounters resistance and cannot be advanced further, the operator can move the expandable segment to the expanded state in which the expandable segment engages an inner surface of the medical device. The expandable segment locks onto the medical device, which allows the guidewire and medical device to be advanced through the vessel together as a single unit. Thus, the stiffness of the guidewire is used to effectively enhance the pushability and hence crossability of a flexible catheter.

According to an embodiment of the present invention, the expandable segment is comprised of an elastic material, such as an elastomeric o-ring, which can be compressed in order to radially expand. According to yet another embodiment of the present invention, the expandable segment is comprised of a balloon that can be inflated in order to radially expand.

According to another aspect of the present invention, a guidewire is provided with a plurality of longitudinally spaced expandable segments. The segments would be designed to impart a longitudinal displacement to the over-riding component with respect to the guidewire. The segments may be activated in such a manner as to "inchworm" an engaged medical device through a body vessel. This is preferred when the guidewire has already been properly positioned at the target site and it is undesirable to advance the guidewire further into the vessel. Such "inchworm" motion is characterized by a leading expandable segment that is typically stationary with respect to the guidewire and a trailing expandable segment that is typically axially movable with respect to the guidewire. Both expandable segments are expanded to engage the medical device, and then the trailing expandable segment is moved toward the leading expandable segment. At this stage, the leading expandable segment is collapsed, which causes the medical device to move through the vessel. Finally, the trailing expandable segment is collapsed and moved away from the leading expandable segment and the process is repeated. This process can be automated or carried out manually.

Special application for the present invention has been found for guidewire delivery of OTW and RX catheters to vessels of the human vascular system. However, the present invention is also applicable to guidewire delivery of stent delivery systems and other medical devices to other body lumens, so it will be understood that the products described herein are not limited to particular medical devices or particular surgical applications.

BRIEF DESCRIPTION OF THE DRAWINGS

FIG. 1 is a cross-sectional view of a prior art double-tube balloon catheter and guidewire;

FIG. 2 is a cross-sectional view of a guidewire according to the present invention disposed within a single-tube balloon catheter in a body vessel;

FIG. 3 is a cross-sectional view of a guidewire with an elastic expandable segment in a collapsed state;

FIG. 4 is a cross-sectional view of the guidewire of FIG. 3 with the expandable segment in an expanded state;

FIG. 5 is a cross-sectional view of another embodiment of a guidewire according to the present invention, with a balloon expandable segment in a collapsed state;

FIG. 6 is a cross-sectional view of the guidewire of FIG. 5 with the expandable segment in an expanded state;

FIG. 7 is a cross-sectional view of the guidewire of FIG. 6 disposed within a single-tube balloon catheter;

FIG. 8 is a cross-sectional view of a guidewire having a locking mechanism; and

FIG. 9 is a cross-sectional view of a guidewire having a plurality of expandable segments.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 2 illustrates the general structure and function of a guidewire 22 according to the present invention, as well as a medical device 24 deliverable with the guidewire 22. The illustrated medical device 24 is an OTW catheter, but the present invention can be applied to RX catheters and other medical devices with a lumen suitable for delivery using a guidewire.

The guidewire 22 has a proximal portion 26 and a distal portion 28 that are separated by expandable segment 30. The proximal portion 26 is relatively rigid for pushing the guidewire 22 to the target site and providing tactile feedback to the operator, while the distal portion 28 includes a tip 32 with a flexible coiled spring for navigation through tortuous body vessels. The proximal and distal portions 26 and 28 may be made of stainless steel, a nitinol, or any other suitable material.

Typically, the expandable segment 30 remains in a collapsed state during use, illustrated in FIG. 3. As shown, the diameter of the expandable segment 30 in a collapsed state is preferably no greater than the diameter of the proximal and distal portions 26 and 28 of the guidewire 22. This allows the guidewire 22 to operate as a standard guidewire when the expandable segment 30 is in a collapsed state.

If there are no difficult-passage locations, such as stenosed or constricted regions, in the path defined by the guidewire 22, then the catheter 24 can be passed over the guidewire 22 and delivered to the target site without activating the expandable segment 30. However, if the guidewire 22 and catheter 24 must traverse a difficult-passage location such as a stenosed region S of a body vessel V, then the expandable segment 30 is radially expanded by active action to move it from the collapsed state of FIG. 3 to the expanded state of FIGS. 2 and 4. As illustrated, the diameter of the expandable segment 30 increases until it engages an inner surface 34 of the catheter 24. Preferably, the expandable segment 30 is sized and configured to expand sufficiently to lock onto the inner surface 34 without damaging the catheter 24.

In order for optimal functionality, a high coefficient of friction should exist between the guidewire expandable segment 30 and catheter inner surface 34; otherwise the catheter 24 will slide away from the expandable segment 30 and resist passage further into the vessel V. Accordingly, the expandable segment 30 may be comprised of a material providing enhanced friction when engaging the inner surface 34. Alternatively, a surface treatment may be provided at and/or applied to the expandable segment 30 or inner surface 34 for enhanced frictional engagement.

The expandable segment 30 is preferably generally adjacent to the flexible tip 32 of the guidewire 22 in order to facilitate engagement of the expandable segment 30 at a distal end of the catheter 24. The problem of a catheter "snaking" against a constricted vessel region is caused by pushing it from a proximal end, so the problem is minimized by causing the expandable segment 30 to actively grip the inner surface 34 at a distal end of the catheter 24 and move the guidewire distally so as to effectively have the guidewire "pull" the catheter through the difficult-passage location of the vascular system.

Preferably, the guidewire 22 is provided with a radiopaque marker 36 for locating and properly positioning the expandable segment 30. Most preferably, the guidewire 22 includes a radiopaque marker 36 at each end of the expandable segment 30 for better locating the expandable segment 30. Alternatively, the expandable segment 30 could be comprised of a radiopaque material or receive a radiopaque surface treatment.

More particularly, when the expandable segment 30 has locked onto the catheter 24, the guidewire 22 is advanced through the vasculature and effectively pulls the catheter 24 through any stenosed or constricted regions S or the like and to the target site. Thus, a guidewire according to the present invention allows for navigation of a flexible catheter through virtually any stenosed region of a body vessel that is navigable by a guidewire.

The expandable segment 30 does not need to grip an entire perimeter of the inner surface 34 in order to function. Preferably, the entire perimeter of the interior surface 34 is gripped by the expandable segment 30 in order to provide a stronger frictional engagement to achieve the needed pulling action.

A further advantage of providing an expandable segment 30 that engages a perimeter of the inner surface 34 is that it allows for the use of a simplified catheter. As illustrated in FIGS. 2 and 7, a simplified catheter 24 having a single outer tube 38 and an inflatable section 40 may be provided. When desired, a stent 41 can be positioned over the inflatable section 40. In contrast to the catheter 10 of FIG. 1, the simplified catheter 24 has no inner body 18 or distal sealing section 20, because the distal end of the inflatable section 40 is sealable by the expandable segment 30 in an expanded state, as shown in FIGS. 2 and 7, with a proximal seal that is achieved by a similar expandable segment 30 proximal of the inflation port or a seal integral to the simplified catheter 24 proximal of the inflation port. The combination of at least two seals will provide a means to create a chamber capable of pressurization to inflate section 40. A prior art catheter such as shown in FIG. 1 typically has a relatively large minimum outer diameter or profile of approximately 0.042 inch.

Due to its simplified design, the catheter 24 may have a smaller outer diameter and decreased stiffness of the inflation section, when compared with a double-tube catheter as shown in FIG. 1. This allows for the delivery of longer stents to hard-to-reach lesions. This also allows for delivery of devices previously not possible due to a variety of reasons such as profile, tortueosity, and bending stiffness. In particular, an outer diameter or profile of approximately 0.032 inch is achievable for current POBA, SDS and DES catheters used with the present guidewire. Such systems are capable of having flexibility similar to that of a fixed wire catheter. However, a guidewire and catheter combination according to the present invention is preferable to a fixed wire catheter, because the present guidewire can be positioned independently of the catheter.

In use, the guidewire 22 and catheter 24 are passed through the vasculature to a target site according to the above-described process. Thereafter, the expandable segment 30 is oriented distally of the inflatable section 40 of the catheter 24 and radially expanded to the expanded state of FIGS. 2 and 7. When a suitable seal has been provided around the perimeter of the inner surface 34, an inflation fluid is introduced to the inflation section 40 through a catheter balloon inflation lumen 42. The inflation fluid causes the inflation section 40 to expand for engagement with the body vessel or for expansion of a stent 41 surrounding the inflation section 40.

FIGS. 3 and 4 illustrate a first embodiment of a guidewire 22a according to the present invention. The guidewire 22a has a proximal portion 26a and a distal portion 28a that are separated by expandable segment 30a. Expandable segment 30a is comprised of an elastic material that is radially expanded from the collapsed state of FIG. 3 to the expanded state of FIG. 4 by axial compression. Preferably, the expandable segment 30a is an elastomeric o-ring. In an illustrated embodiment, the o-ring has an inner diameter of approximately 0.010 inch and an outer diameter of approximately 0.014 inch. A full ring is not necessary, provided that the elastic material of the expandable segments is capable of expanding to provide sufficient friction against a medical device, but a full ring is preferred in order to create a complete perimeter seal, which allows the use of a simplified catheter, as described above.

In order to axially compress the o-ring 30a, the proximal portion 26a and the distal portion 28a are movable relative to each other. The proximal portion 26a is substantially tubular and movably receives a shaft extension 44 of the distal portion 28a. The outer diameter of the proximal and distal portions 26a and 28a in the illustrated embodiment are approximately 0.014 inch to coincide with the outer diameter of the o-ring 30a in the collapsed state of FIG. 3. The shaft 44 extends through the center of the o-ring 30a and proximal portion 26a and terminates in a diameter ramp-up section 46 located proximally of the proximal portion 26a. The outer diameter of the diameter ramp-up section 46 is greater than the inner diameter of the proximal portion 26a, which prevents excess movement of the distal portion 28a away from the proximal portion 26a.

In order to actively radially expand the o-ring 30a, the diameter ramp-up section 46 or a handle associated with the diameter ramp-up section 46, not illustrated, is moved proximally or upstream from the position of FIG. 3 to the position of FIG. 4 or to an intermediate position between those illustrated in FIGS. 3 and 4. Proximal or upstream movement of the diameter ramp-up section 46 also moves the shaft 44 and distal portion 28a proximally or upstream with respect to the proximal portion 26a of the guidewire 22a. The resulting movement of the distal portion 28a closer to the proximal portion 26a compresses the o-ring 30a and causes it to radially expand until it engages an inner surface of a surrounding medical device, as generally shown in FIG. 2. The distal portion 28a is thereafter moved away from the proximal portion 26a in order to return the o-ring 30a to its collapsed state and proceed with further medical treatment action as desired.

Preferably, the guidewire includes a locking mechanism for selectively preventing movement from the orientation of FIG. 4 to the orientation of FIG. 3. One possible locking mechanism is achieved by providing a guidewire 22a' having a threaded shaft length 44' with threads that mate with a proximal portion threaded length 26a' of the guidewire 22a', as illustrated in FIG. 8. This allows for axial advancement of the shaft 44' by rotation, in addition to serving as a locking mechanism.

In a preferred arrangement for such a locking mechanism, the threaded lengths are coordinated so that the shaft and guidewire engage each other to prevent any further axial movement in the distal direction that would cause excess compression of the expandable segment 30a and possible damage to the expandable segment or otherwise damage the distal portion of the device. For example, a radially extending proximal edge 53 of the shaft 44' can engage a radially extending distal edge 54 of the ramp-up section 46 precisely when the expandable segment 30a is expanded to the maximum or optimum extent.

Other suitable locking mechanisms include a ratcheting member associated with diameter ramp-up section 46. This can include markings or other indicators (not shown) that correspond to a degree or degrees of rotation needed to achieve one or more levels of expansion of the expandable segment. Other locking mechanisms may also be used without departing from the scope of the present invention.

FIGS. 5-7 illustrate another embodiment of a guidewire according to the present invention. The guidewire generally designated as 22b has a proximal portion 26b and a distal portion 28b that are separated by expandable segment 30b. Expandable segment 30b can take the form of a balloon that is radially expanded from the collapsed state of FIG. 5 to the expanded state of FIGS. 6 and 7 by inflation. The preferred embodiment includes a balloon 30b that is inflatable to engage a complete perimeter of a lumen or inner surface 34 of a catheter 24, which allows the use of a simplified standard catheter design, as described above. However, the balloon 30b could instead expand to engage a smaller portion of the inner surface 34, provided that it supplies sufficient friction.

The illustrated guidewire 22b is further provided with a removable luer 48, a guidewire inflation lumen 50, and an inflation chamber 52 in fluid communication with the guidewire inflation lumen 50. An inflation fluid, typically a saline solution, is injected into the guidewire inflation lumen 50 from a syringe, not illustrated, and the inflation fluid fills the inflation chamber 52 in order to inflate the balloon 30b and radially expand it from the collapsed state of FIG. 5 to the expanded state of FIGS. 6 and 7. Thereafter, the inflation fluid may be removed from the guidewire 22b in order to deflate the balloon 30b and return it to the collapsed state of FIG. 5.

Preferably, the guidewire 22b includes a locking mechanism for selectively preventing unintentional deflation of the balloon 30b. Means for preventing the premature deflation of a balloon catheter and the like are well known to those skilled in the art and may be applied to a guidewire 30b according to the present invention as a suitable locking mechanism. Examples for this embodiment are known mechanisms for applying inflation pressure to the inflation fluid which apply the pressure to the fluid at a desired level so as to achieve and maintain balloon inflation levels that are maximal and/or optimal for the particular device and use. As for the locking mechanism of the o-ring embodiment, the locking mechanism for the balloon embodiment can be arranged so as to control expansion and stop such expansion when a selected extent of expansion has been attained and overexpansion has been avoided.

The illustrated embodiments of FIGS. 2-7 show a guidewire having a single expandable segment, but a guidewire having a plurality of expandable segments 30c, 30d also is within the scope of the present invention. The expandable segments are designed to impart a longitudinal displacement to the ID of the component. The expandable segments may be disposed at different positions along the length of the guidewire 22b, as shown in FIG. 9, and/or at different angular locations. The expandable segments need not be identical, but may be differently sized and/or shaped, and a combination of balloons and o-rings may also be employed. The various expandable segments may be actuated simultaneously, e.g., by providing a plurality of balloons associated with a single inflation lumen according to the embodiment of FIG. 9, or independently of each other, or in series. Typically, inflation will be controlled by the surgeon so as to effect an "inchworm" type of action. Automated operation could be possible, especially when the segments are activated in series.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A guidewire for interluminal delivery to a body vessel of a medical device having an inner surface, comprising:
    a substantially tubular guidewire portion having a distal end that has a radially extending face and a proximal end that has a radially extending face;
    a distal guidewire shaft portion slidably movable with respect to the tubular guidewire portion and including a shaft extension which is slidably movably received within the tubular guidewire portion and extends beyond both ends of the tubular guidewire portion;
    the end of the shaft extension that extends distally beyond the tubular guidewire portion has a first diameter ramp up section having a radially extending opposing face disposed opposite the radially extending face of the tubular guidewire portion distal end;
    the end of the shaft extension that extends proximally beyond the tubular guidewire portion has a second diameter ramp up section having a radially extending face disposed opposite the radially extending face of the tubular-guidewire portion proximal end;
    a length of the distal guidewire shaft portion, said length is circumferentially indented with respect to both of and extends between the first and second diameter ramp up sections;
    an expandable segment of the guidewire that is disposed intermediate said radially extending face of the tubular guidewire portion and said opposing face of the distal guidewire portion;
    the expandable segment being an elastomeric o-ring and movable between a collapsed state and a radially expanded state, wherein relative axial movement of the tubular guidewire portion and the shaft extension of the distal guidewire portion with respect to each other axially compresses said expandable segment to place the expandable segment between said faces in the radially expanded state for engaging at least a portion of an inner surface of a medical device for movement of the medical device with said expandable segment within a body vessel;
    a first annular radiopaque marker between the radially extending face of the tubular guidewire portion and a first side of the elastomeric o-ring;
    a second annular radiopaque marker between the radially extending opposing face of the first diameter ramp up section and a second side of the elastomeric o-ring opposite to the first side of the O-ring;
    each of said tubular guidewire portion, said expandable segment, said first annular radiopaque marker and said second annular radiopaque marker overlies only said circumferentially indented length of the distal guidewire shaft portion, and each does not extend radially beyond the diameter ramp up sections; and
    a locking mechanism between said tubular guidewire portion and said shaft extension for selectively preventing said expandable segment from moving from said radially expanded state to said collapsed state while the locking mechanism is engaged.

2. The guidewire of claim 1, wherein said locking mechanism selectively prevents said expandable segment from expanding beyond a preselected optimal expansion extent.

3. The guidewire of claim 1, further comprising a plurality of expandable segments.

4. The guidewire of claim 1, wherein said expandable segment is engageable with a distal end of a medical device balloon catheter.

5. A guidewire for delivery through a body vessel of a medical device that is positioned over the guidewire, the guidewire comprising:
    a substantially tubular guidewire portion having a distal end that has a radially extending face and a proximal end that has a radially extending face;
    a distal guidewire shaft portion slidably movable with respect to the tubular guidewire portion and including a shaft extension which is slidably movably received within the tubular guidewire portion and extends beyond both ends of the tubular guidewire portion;
    the end of the shaft extension that extends distally beyond the tubular guidewire portion has a first diameter ramp up section having a radially extending opposing face disposed opposite the radially extending face of the tubular guidewire portion distal end;

the end of the shaft extension that extends proximally beyond the tubular guidewire portion has a second diameter ramp up section having a radially extending face disposed opposite the radially extending face of the tubular-guidewire portion proximal end;

a length of the distal guidewire shaft portion, said length is circumferentially indented with respect to both of and extends between the first and second diameter ramp up sections;

an expandable segment of the guidewire that is disposed intermediate said radially extending face of the tubular guidewire portion and said opposing face of the distal guidewire portion, wherein said expandable segment is an elastomeric o-ring and is movable between a collapsed state and an expanded state upon relative axial movement of the tubular guidewire portion and the shaft extension of the distal guidewire portion, and wherein, when said guidewire is positioned within a medical device having an inner surface, said expandable segment in said expanded state is axially compressed between said opposing faces of the guidewire portions and radially expanded to engage at least a portion of the inner surface of the medical device for longitudinal movement within a body vessel of the medical device together with said expandable segment;

a first annular radiopaque marker between the radially extending face of the tubular guidewire portion and a first side of the elastomeric o-ring;

a second annular radiopaque marker between the radially extending opposing face of the first diameter ramp up section and a second side of the elastomeric o-ring opposite to the first side of the o-ring;

each of said tubular guidewire portion, said expandable segment, said first annular radiopaque marker and said second annular radiopaque marker overlies only said circumferentially indented length of the distal guidewire shaft portion, and each does not extend radially beyond the diameter ramp up sections; and a locking mechanism between said tubular guidewire portion and said shaft extension for selectively preventing said expandable segment from moving from said expanded state to said collapsed state while the locking mechanism is engaged.

6. The guidewire of claim 5, wherein said locking mechanism selectively prevents said expandable segment from moving from said expanded state to an overexpanded state.

7. The guidewire of claim 5, further comprising a plurality of expandable segments.

8. The guidewire of claim 5, wherein said expandable segment is engageable with a distal end of a medical device angioplasty catheter having stent delivery capabilities.

* * * * *